(12) United States Patent
West et al.

(10) Patent No.: US 10,967,389 B2
(45) Date of Patent: Apr. 6, 2021

(54) SYSTEMS AND METHODS FOR AUTOMATICALLY BALANCING A CENTRIFUGE

(71) Applicant: Fenwal, Inc., Lake Zurich, IL (US)

(72) Inventors: Richard L. West, Lake Villa, IL (US); Daniel R. Lynn, Spring Grove, IL (US)

(73) Assignee: Fenwal, Inc., Lake Zurich, IL (US)

( * ) Notice: Subject to any disclaimer, the term of this patent is extended or adjusted under 35 U.S.C. 154(b) by 845 days.

(21) Appl. No.: 15/358,200

(22) Filed: Nov. 22, 2016

(65) Prior Publication Data
US 2017/0144172 A1    May 25, 2017

Related U.S. Application Data (60) Provisional application No. 62/258,781, filed on Nov. 23, 2015.

(51) Int. Cl.
*B04B 9/14* (2006.01)
*B04B 5/04* (2006.01)
(Continued)

(52) U.S. Cl.
CPC ............. *B04B 9/14* (2013.01); *A61M 1/3693* (2013.01); *B04B 5/0442* (2013.01); *B04B 9/12* (2013.01); *B04B 2005/0492* (2013.01)

(58) Field of Classification Search
CPC ........... B04B 9/14; B04B 5/0442; B04B 9/12; B04B 2005/0492; A61M 1/3693
(Continued)

(56) References Cited

U.S. PATENT DOCUMENTS 3,834,613 A * 9/1974 Hankey ............... B04B 9/14
                                                  494/16
3,986,442 A * 10/1976 Khoja ................ B04B 5/0442
                                                  475/182
(Continued)

FOREIGN PATENT DOCUMENTS

EP    2 397 228 A2    12/2011

OTHER PUBLICATIONS

Extended European Search Report for European Patent Appln. No. 16199981.8, dated Mar. 28, 2017.

*Primary Examiner* — Walter D. Griffin
*Assistant Examiner* — Shuyi S. Liu
(74) *Attorney, Agent, or Firm* — Cook Alex Ltd.

(57) ABSTRACT

A centrifuge rotor assembly includes a chamber assembly, a bearing support, and a counterweight that is substantially diametrically opposed to the bearing support with respect to the chamber assembly. The chamber assembly receives a processing chamber of a fluid circuit, while the bearing support receives a portion of an umbilicus that is fluidly connected to the processing chamber. The bearing support and counterweight are rotated about a central axis of the chamber assembly by an electric drive of the centrifuge rotor assembly, with the bearing support and counterweight remaining substantially diametrically opposed to each other with respect to the chamber assembly while being rotated about the central axis. The electric drive may rotate the bearing support and counterweight at a plurality of different speeds, with the counterweight automatically moving with respect to the bearing support between radially innermost and radially outermost positions to balance the centrifuge rotor assembly.

23 Claims, 8 Drawing Sheets

(51) Int. Cl.
*A61M 1/36* (2006.01)
*B04B 9/12* (2006.01)

(58) Field of Classification Search
USPC ........ 604/5.01; 475/11, 182; 494/21, 18, 83,
494/84; 474/86, 150
See application file for complete search history.

(56) References Cited

U.S. PATENT DOCUMENTS

| | | |
|---|---|---|
| 4,120,449 A | 10/1978 | Brown et al. |
| 4,157,781 A | 6/1979 | Maruyama |
| 4,776,832 A * | 10/1988 | Martin ..................... B04B 5/02 |
| | | 494/19 |
| 4,919,646 A | 4/1990 | Perdriat |
| 5,376,063 A | 12/1994 | Greenstein |
| 5,996,634 A | 12/1999 | Dennehey et al. |
| 7,285,085 B2 | 10/2007 | Kim et al. |
| 7,819,792 B2 | 10/2010 | Ryu et al. |
| 2010/0009831 A1 * | 1/2010 | Ryu ....................... B04B 9/146 |
| | | 494/8 |
| 2010/0089200 A1 * | 4/2010 | Sappenfield ........ F16H 37/0813 |
| | | 74/665 Q |
| 2011/0306913 A1 * | 12/2011 | West .................... B04B 5/0442 |
| | | 604/5.01 |
| 2015/0122977 A1 * | 5/2015 | Halvorsen .......... G01N 15/1436 |
| | | 250/214.1 |

* cited by examiner

SYSTEMS AND METHODS FOR AUTOMATICALLY BALANCING A CENTRIFUGE

CROSS REFERENCE TO RELATED APPLICATIONS

This application claims the benefit of and priority of U.S. Provisional Patent Application Ser. No. 62/258,781, filed Nov. 23, 2015, the contents of which are incorporated by reference herein.

BACKGROUND

Field of the Disclosure

The present disclosure relates to centrifugal fluid separation systems. More particularly, the present disclosure relates to systems and methods for automatically balancing a centrifuge.

Description of Related Art

Whole blood is routinely separated into its various components, such as red blood cells, platelets, and plasma. In typical blood processing systems, whole blood is drawn from a source, the particular blood component or constituent is removed and collected, and the remaining blood constituents are returned to the source or to a different recipient. If the source is a human or animal donor, an advantage of such a procedure is that less time is needed for the donor's body to return to normal, and donations can be made at more frequent intervals than when whole blood is collected. This increases the overall supply of blood constituents, such as plasma and platelets, made available for health care.

Whole blood is typically separated into its constituents through centrifugation. This requires that the whole blood be passed through a centrifuge after it is withdrawn from the source and before it is pumped to the recipient. To avoid contamination, the blood is usually contained within a sealed, sterile system during the entire centrifugation process. Typical blood processing systems thus include a permanent, reusable centrifuge assembly or "hardware" that spins and pumps the blood, and a disposable, sealed and sterile fluid circuit that actually makes contact with the blood. The centrifuge assembly receives and spins a portion of the fluid circuit (which may be referred to as a processing chamber) during a collection procedure, with the blood separating into its constituent parts within the processing chamber. After use, the fluid circuit is typically discarded, while the centrifuge assembly may be used again with new fluid circuits.

To avoid the need for rotating seals, and to preserve the sterile and sealed integrity of the fluid circuit, blood processing systems often utilize centrifuges that operate on the "one-omega, two-omega" operating principle. This principle is disclosed in detail in U.S. Pat. No. 4,120,449 to Brown et al., which is hereby incorporated by reference, and enables centrifuges to spin a sealed, closed fluid circuit without the need for rotating seals and without twisting the components of the fluid circuit. Blood processing systems that make use of the principle typically include a fluid circuit that includes a processing chamber that is spun in the centrifuge and that is connected to the blood source and to a stationary portion of the centrifuge assembly through an elongated member that may be made up of one or more plastic tubes. The elongated member is commonly referred to as an "umbilicus" and is typically arranged in a question mark (or upside-down question mark) configuration with both of its end portions coaxially aligned with the axis of rotation of the centrifuge. The centrifuge chamber is rotated at "two-omega" RPM and the umbilicus is orbited around the centrifuge chamber at "one-omega" RPM. In other words, one end of the umbilicus is stationary, the other end rotates at a two-omega speed with the centrifuge chamber to which it is attached, and the intermediate portion or midsection of the umbilicus orbits about the chamber at a one-omega speed. The effect is that the end of the umbilicus, which is opposite the bag or chamber and is connected to the source via plastic tubing, does not twist up as the bag is spun. The sealed, sterile integrity of the fluid circuit is thus maintained without the need for rotating seals.

One challenge associated with centrifuge assemblies is balancing them during use. If the centrifuge assembly is not balanced, then it may operate irregularly (e.g., vibrating or wobbling), which may affect the separation of blood, as well as potentially damaging the hardware. Existing umbilicus-based centrifugation systems are typically provided with a counterweight that is positioned across from the umbilicus to help balance the centrifuge assembly, but the imbalancing effect of the umbilicus may vary during use, so there remains the need for an improved system of balancing an umbilicus-based centrifuge assembly.

SUMMARY

There are several aspects of the present subject matter, which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a centrifuge rotor assembly includes a chamber assembly, a bearing support, a counterweight, and an electric drive. The chamber assembly has a central axis and is configured to receive at least a portion of a processing chamber of a fluid circuit. The bearing support is configured to receive a portion of an umbilicus fluidly connected to the processing chamber, while the counterweight is positioned substantially diametrically opposed to the bearing support with respect to the chamber assembly. The electric drive is configured to rotate the bearing support and the counterweight about the central axis at a plurality of different rotational speeds, with the bearing support and the counterweight remaining substantially diametrically opposed to each other with respect to the chamber assembly during rotation. The counterweight is automatically movable with respect to the bearing support between a radially innermost position and a radially outermost position during rotation, with the position of the counterweight depending at least in part on the rotational speed at which the bearing support and the counterweight are rotated about the central axis.

In another aspect, a method is provided for operating a centrifuge rotor assembly having a chamber assembly that receives at least a portion of a processing chamber of a fluid circuit, a bearing support receiving a portion of an umbilicus fluidly connected to the processing chamber, and a counterweight positioned substantially diametrically opposed to the bearing support with respect to the chamber assembly. The method includes rotating the bearing support and the counterweight about a central axis of the chamber assembly at a first rotational speed while the bearing support and the counterweight remain substantially diametrically opposed to each other with respect to the chamber assembly. The rotational speed is changed from the first rotational speed to a second rotational speed while the bearing support and the counterweight remain substantially diametrically opposed to each other with respect to the chamber assembly. Changing the rotational speed to the second rotational speed includes automatically moving the counterweight with respect to the bearing support from a first radial position to a second radial position, with the radial position of the counterweight depending at least in part on the rotational speed at which the bearing support and the counterweight are rotated about the central axis.

DESCRIPTION OF THE ILLUSTRATED EMBODIMENTS

The embodiments disclosed herein are for the purpose of providing an exemplary description of the present subject matter. They are, however, only exemplary, and the present subject matter may be embodied in various forms. Therefore, specific details disclosed herein are not to be interpreted as limiting the subject matter as defined in the accompanying claims.

Figure 1:
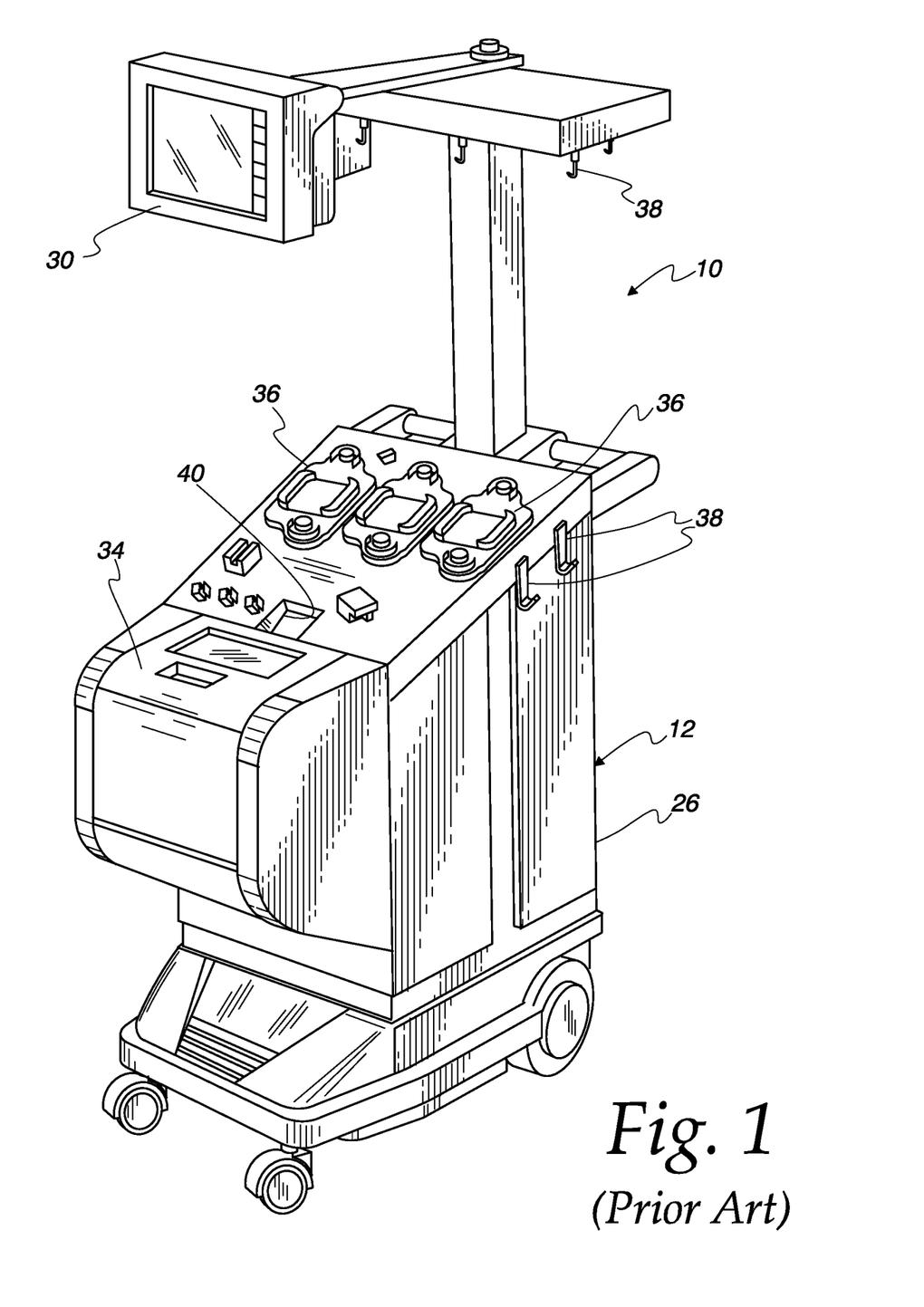
FIG. 1 is a perspective view of a durable fluid processing system according to conventional design.

FIG. 1 shows an umbilicus-based centrifugal fluid processing system 10 according to conventional design. The system 10 can be used for processing various fluids, but is particularly well suited for processing whole blood, blood components, or other suspensions of biological cellular materials. The system 10 includes a centrifuge assembly 12 for separating a fluid into its constituent parts. A more detailed description of the centrifuge assembly 12 and the other elements of the system 10 can be found in U.S. Pat. No. 5,996,634, which is incorporated by reference herein.

Figure 2:
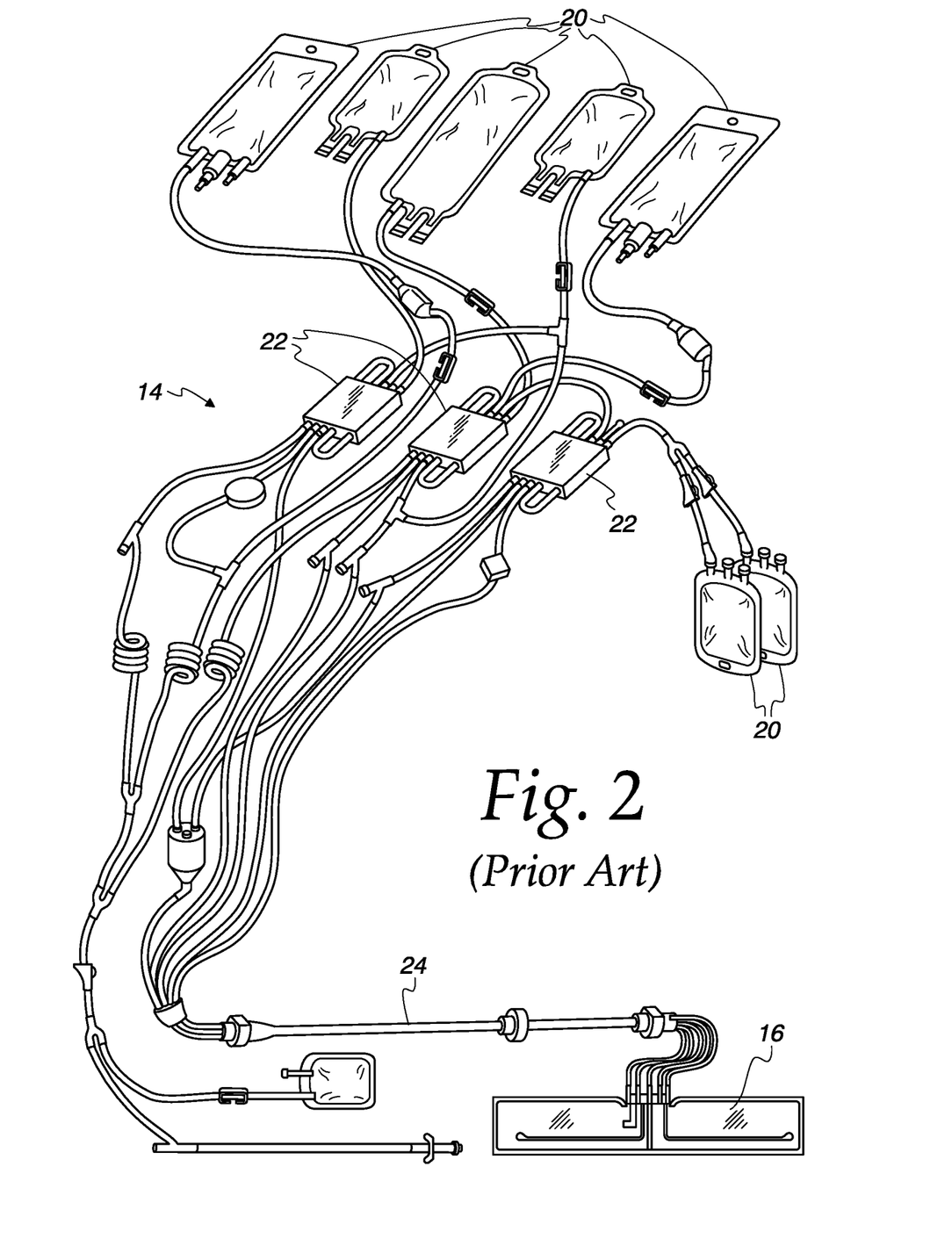
FIG. 2 is a perspective view of a disposable fluid circuit according to conventional design that is usable in association with the durable fluid processing system of FIG. 1.
Figure 3:
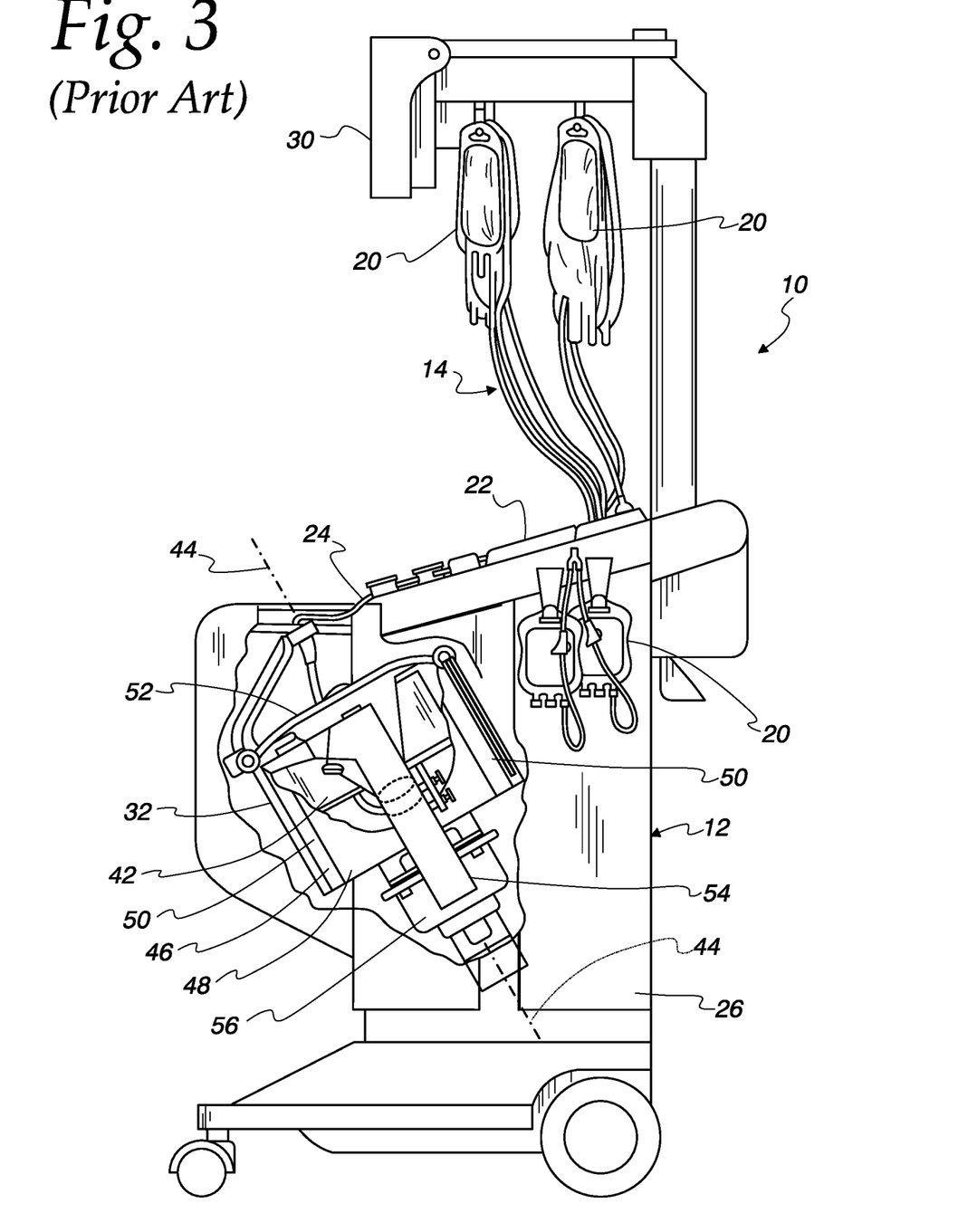
FIG. 3 is a side elevational view of the disposable fluid circuit of FIG. 2 mounted on the durable fluid processing system of FIG. 1, which is partially broken away for illustrative purposes.

The durable fluid processing system 10 is used in combination with a disposable fluid circuit 14, an example of which is shown in FIG. 2. FIG. 3 shows the disposable fluid circuit 14 mounted on the durable system 10. The disposable fluid circuit 14 is a preferably single use, disposable item loaded on the system 10 at the time of use. After a fluid processing procedure has been completed, the operator preferably removes the disposable fluid circuit 14 from the system 10 and discards it.

The disposable fluid circuit 14 includes a processing chamber 16 (FIG. 2). In use, the centrifuge assembly 12 rotates the processing chamber 16 to centrifugally separate blood components. Whole blood is conveyed to the processing chamber 16, and separated blood components are conveyed from the processing chamber 16, through a plurality of flexible tubes. The fluid circuit 14 further includes a plurality of containers 20 that may be supported by elevated hangers located over the centrifuge assembly 12 (see FIG. 3) and that dispense and receive liquids during processing. Fluid flow through the fluid circuit 14 may be controlled in a variety of ways. Preferably, fluid flow is controlled via cassettes 22 with pre-formed fluid passageways, which may be selectively opened and closed pneumatically, hydraulically, or by movable actuators. The number of cassettes may vary, but in the illustrated embodiment, there are three cassettes 22, which operate in association with valve and pump stations on the centrifuge assembly 12 to direct liquid flow among multiple liquid sources and destinations during a blood processing procedure. Tubes connected to the processing chamber 16 lead to a flexible umbilicus 24, with additional tubes at the other end of the umbilicus 24 fluidly connecting the processing chamber 16 (via the umbilicus 24) to the remainder of the disposable fluid circuit 14, including the containers 20 and the cassettes 22. Advantageously, the disposable fluid circuit 14 is a pre-assembled closed system, assuring an operator that it is a sterile unit.

As illustrated, the centrifuge assembly 12 includes a wheeled cabinet 26 that can be easily rolled from place to place. A user-actuable processing controller 30 is provided, which enables the operator to control various aspects of the blood processing procedure. A centrifuge rotor assembly 32 is provided behind a fold-open door 34 that can be pulled open at the front of the cabinet 26 (FIG. 3). A plurality of valve and pump stations 36 (FIG. 1) are provided on the top face of the cabinet for receiving and controlling the various cassettes 22. A plurality of hooks or hangers 38 is provided on the cabinet 26 for suspending the various containers 20.

Figure 4:
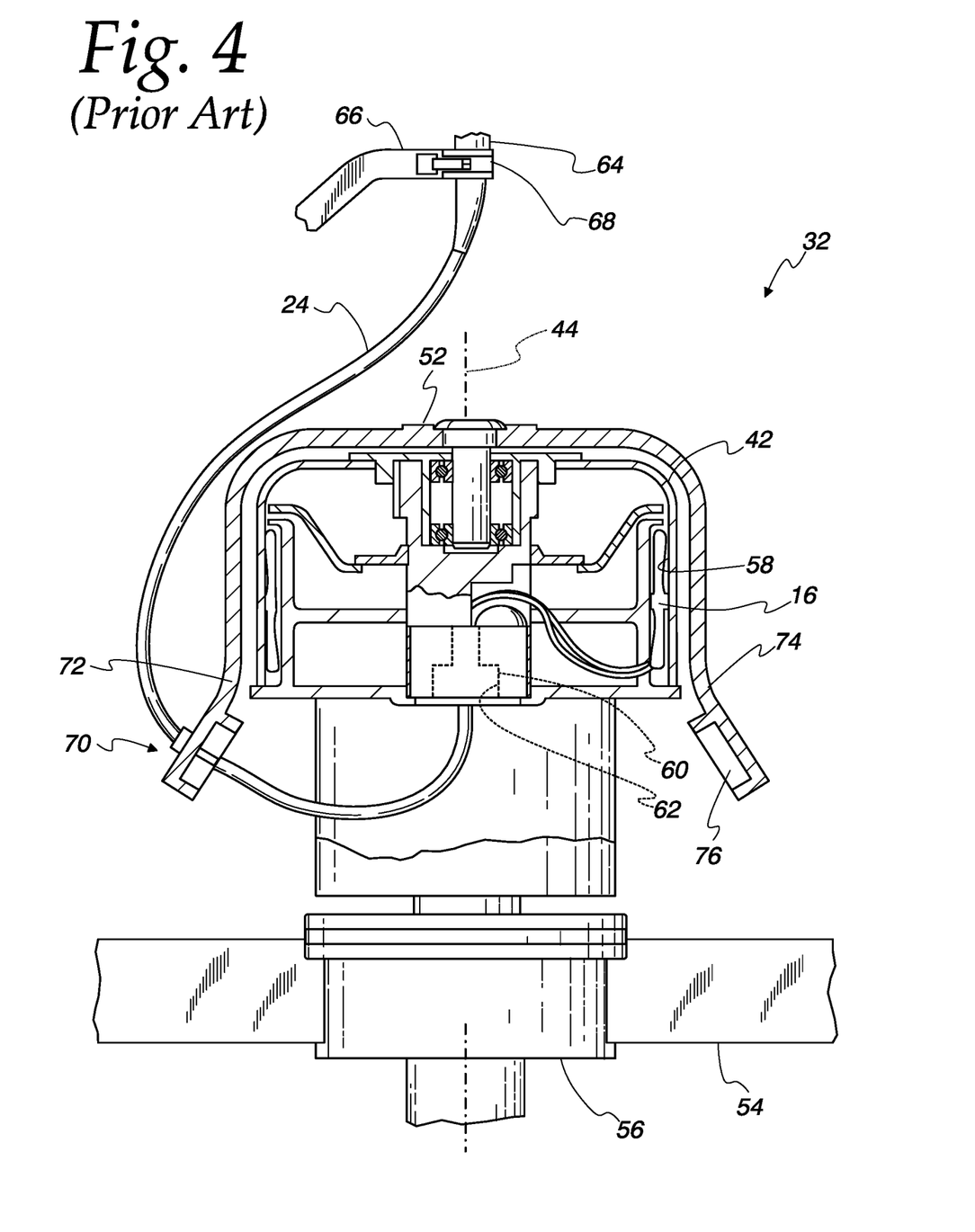
FIG. 4 is a side detail view of a centrifuge included in the durable fluid processing system of FIG. 1, showing the centrifuge in combination with an umbilicus of the disposable fluid circuit.

In use, the fold-open door 34 is opened and the processing chamber 16 of the disposable fluid circuit 14 is mounted in the centrifuge rotor assembly 32 (FIG. 4). The umbilicus 24 is threaded through the centrifuge rotor assembly 32 and out through an opening 40 in the upper panel of the cabinet 26 (FIG. 3). Each cassette 22 is snapped into place within a different one of the valve and pump stations 36, while the containers 20 are hung from the appropriate hangers 38 (FIG. 3). After appropriate connections are made to the blood source, the operator enters appropriate commands on the processing controller 30 to begin the processing procedure.

Looking more closely at the centrifuge rotor assembly 32 (FIG. 4), it includes a chamber assembly 42 that is supported for rotation around a central axis or axis of centrifugation 44. The centrifuge further includes a centrifuge yoke assembly 46 that includes a yoke base 48, a pair of upstanding yoke arms 50, and a yoke cross member 52 mounted between the arms 50. The yoke base 48 is rotatably supported on a stationary platform 54 that carries the rotating mass of the centrifuge rotor assembly 32. The yoke base 48 is also supported for rotation around the axis of centrifugation 44 independently of the chamber assembly 42. An electric drive 56 rotates the yoke assembly 46 relative to the stationary platform 54 around the axis of centrifugation 44. The chamber assembly 42 is free to rotate around the axis of centrifugation 44 at a rotational speed that is different from the rotational speed of the yoke assembly 46.

Referring further to FIG. 4, the chamber assembly 42 defines an annular chamber 58, centered around the axis of centrifugation 44, for receiving the processing chamber 16 of the disposable fluid circuit 14. The umbilicus 24 extends through the lower center of the chamber assembly 42 in alignment with the axis of centrifugation 44. A first anchor portion 60 integrally molded or otherwise mounted onto the umbilicus 24 is received in a lowermost umbilicus mount 62 located at the lower center of the chamber assembly 42. The first anchor portion 60 and umbilicus mount 62 function to transfer torque between the umbilicus 24 and chamber assembly 42 so that the chamber assembly 42 rotates around the axis of centrifugation in response to twisting of the umbilicus 24 around its axis.

The other end of the umbilicus 24 is supported by means of a second anchor portion 64 that is removably received in an upper umbilicus mount 66 positioned over the centrifuge chamber assembly 42 substantially in alignment with the axis of centrifugation 44. An over-center clamp 68 at the end of the upper umbilicus mount 66 clamps onto the second anchor portion 64 to hold the adjacent segment of the umbilicus 24 rotationally stationary and in collinear alignment with the axis of centrifugation 44. The second anchor portion 64 may be integrally molded or otherwise securely joined with the umbilicus 24.

As further illustrated in FIG. 4, the portion of the umbilicus 24 between the second anchor portion 64 and the first anchor portion 60 is supported by a middle umbilicus mount or bearing support 70 that is carried at the lower end of a wing plate 72 extending outwardly and downwardly from the yoke cross member 52. As the electric drive 56 rotates the centrifuge yoke assembly 46 (FIG. 3) around the axis of centrifugation 44, the wing plate 72 and the bearing support 70 pull the midsection of the umbilicus 24 around the axis of centrifugation 44 as well. As the umbilicus 24 orbits around the axis 44, at rotational speed one-omega, a twisting action is imparted to the umbilicus 24 around its own axis. The midsection of the umbilicus 24 is free to rotate around its own axis relative to the wing plate 72 as the yoke assembly 46 is turned, so it will tend to "untwist" against the twisting motion imparted by the rotating yoke assembly 46. As it untwists in this manner, the umbilicus 24 spins the centrifuge chamber assembly 42 around the axis of centrifugation 44 at an average rotational speed of two-omega.

To maintain balance as the yoke assembly 46 turns, an additional wing plate 74 extends from the yoke cross member 52 substantially diametrically opposite the wing plate 72. A counterweight 76 sufficient to balance the mass of the bearing support 70 and umbilicus 24 is carried on the lower end of the additional wing plate 74. By providing a yoke cross member 52 as illustrated that is rotated about the central axis 44, the bearing support 70 and counterweight 76 remain substantially diametrically opposed with respect to the chamber assembly 42 during rotation.

Figure 5:
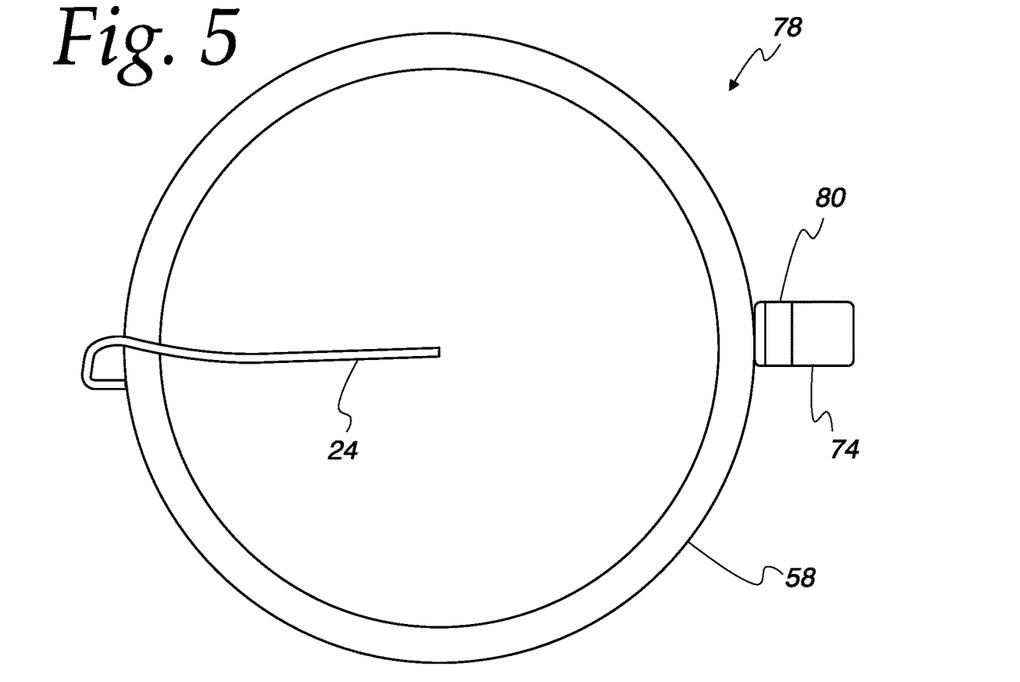
FIG. 5 is a top plan view of a centrifuge assembly incorporating a movable counterweight according to an aspect of the present disclosure, with the counterweight being positioned in a radially innermost position.
Figure 6:
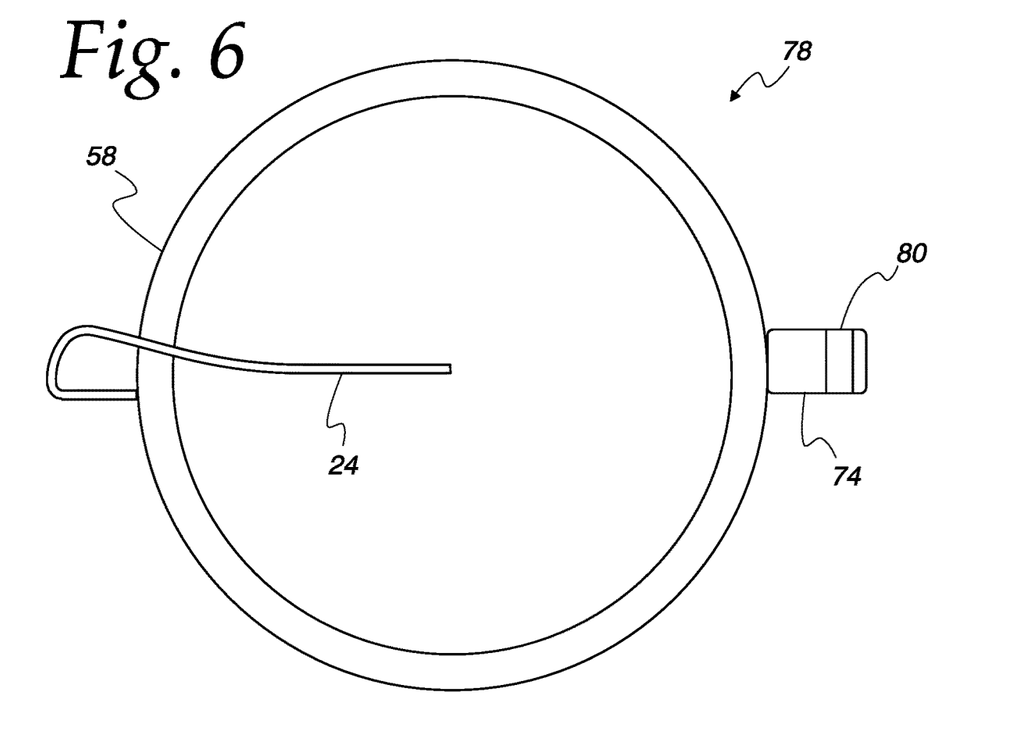
FIG. 6 is a top plan view of the centrifuge assembly of FIG. 5, with the counterweight being positioned in a radially outermost position.

FIGS. 5 and 6 illustrate a variation of the centrifuge rotor assembly 32. The centrifuge rotor assembly 78 of FIGS. 5 and 6 may be configured generally according to the foregoing description of the centrifuge rotor assembly 32, but with the stationary counterweight 76 being replaced by an automatically movable counterweight 80. As shown in FIGS. 5 and 6, the counterweight 80 is movable between a radially innermost position (FIG. 5) and a radially outermost position (FIG. 6), with the radial position of the counterweight 80 depending at least in part on the speed at which the electric drive 56 rotates the yoke cross member 52. The mechanism by which the counterweight 80 moves with respect to the bearing support 70 and umbilicus 24 may vary without departing from the scope of the present disclosure, with a number of exemplary mechanisms being described herein.

It should be understood that the two positions of FIGS. 5 and 6 merely represent the outer bounds of the range of motion of the counterweight 80. The counterweight 80 will pass through intermediate positions (in which the counterweight 80 is farther from the central axis 44/bearing support 70 than in the radially innermost position, but closer to the central axis 44/bearing support 70 than in the radially outermost position) when moving from the radially innermost position to the radially outermost position as the rotational speed is increased from a minimum rotational speed to a maximum rotational speed (as in FIG. 7). Similarly, the counterweight 80 will pass through intermediate radial positions when moving from the radially outermost position to the radially innermost position as the rotational speed decreases from a maximum rotational speed to a minimum rotational speed (as in FIG. 8).

Figure 5A:
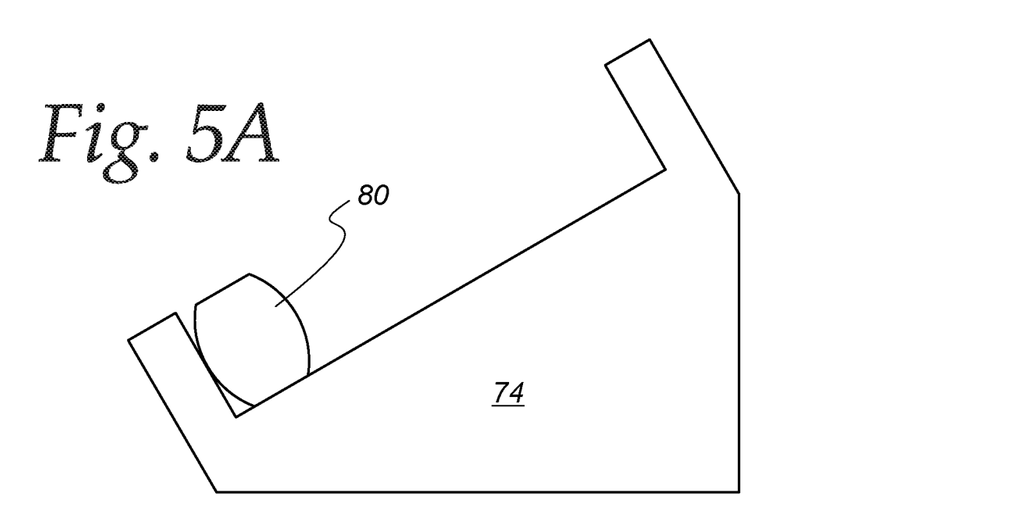
FIG. 5A illustrates a counterweight that is movable along a path having an axial component.
Figure 5B:
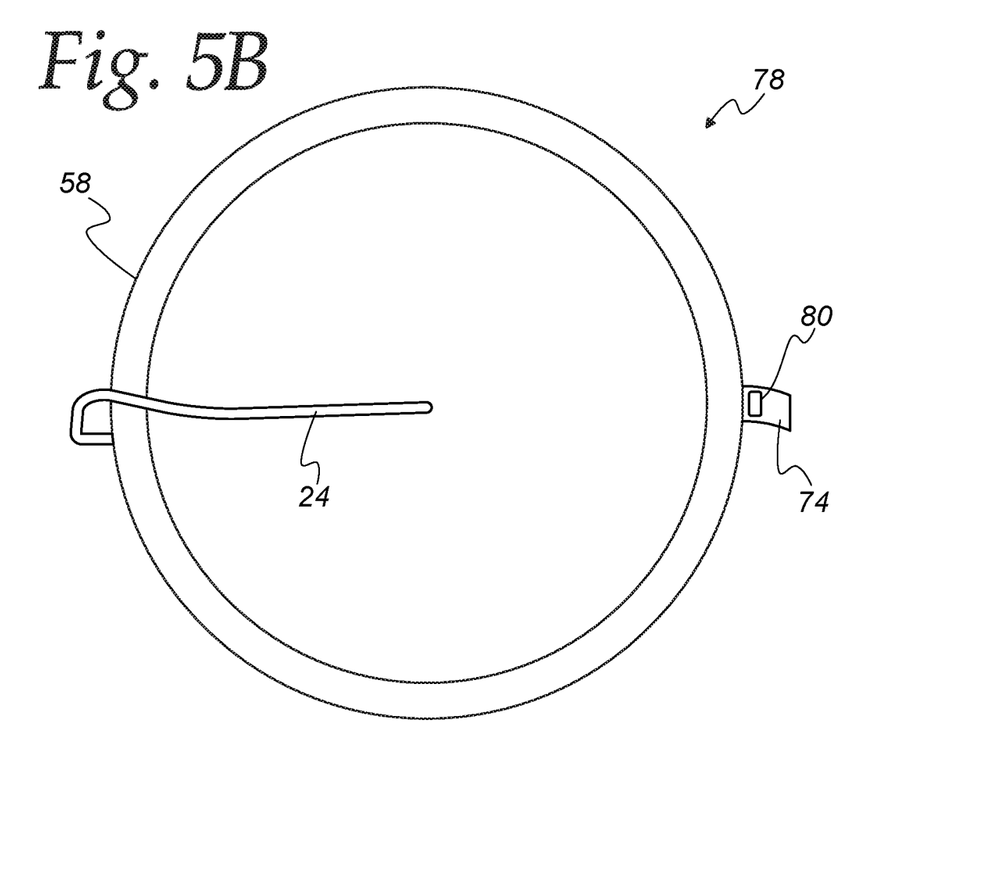
FIG. 5B is a top plan view of a centrifuge assembly incorporating a movable counterweight according to an aspect of the present disclosure, with the counterweight being movable along a non-linear path.

While the counterweight 80 is configured to move between radially innermost and outermost positions, it should be understood that the counterweight 80 is not limited to movement in a strictly radial direction. For example, in addition to moving radially, the counterweight 80 may also move in a direction having an axial component when moving to a more radially outward or more radially inward position. This may include moving the counterweight 80 in a direction having a component that is parallel to the central axis 44 (i.e., upwardly or downwardly in the orientation of FIG. 4) while at the same time moving the counterweight 80 radially with respect to the central axis 44, resulting in an overall diagonal path of travel with respect to vertical (as shown in FIG. 5A). This may be advantageous to counteract any tendency of the umbilicus 24 to shift in an axial direction when moving from one rotational speed to another. Furthermore, the counterweight 80 is not limited to movement through a linear path, but may move along a non-linear (e.g., arcuate) path in traveling between its radially innermost and radially outermost positions (as shown in FIG. 5B), which may be advantageous in counteracting the tendency of the umbilicus 24 to imbalance the centrifuge rotor assembly 78, depending on the behavior of the umbilicus 24 at different rotational speeds.

In one embodiment, the radial position of the counterweight 80 between the radially innermost and outermost positions is infinitely adjustable (i.e., the counterweight 80 may be moved to and remain in any position between the radially innermost and radially outermost positions). In another embodiment, the counterweight 80 is completely movable between the radially innermost and radially outermost positions, but is positionable in only a defined number of positions therebetween. For example, the counterweight 80 may be selectively retained in only five locations—the radially outermost position, the radially innermost position, and three intermediate locations between the radially outermost and innermost positions. The most advantageous configuration may depend upon the behavior of the umbilicus 24 at different rotational speeds during use, along with other factors (e.g., the cost and/or complexity of the system and/or the space available to accommodate components of the counterweight movement system).

Figure 7:
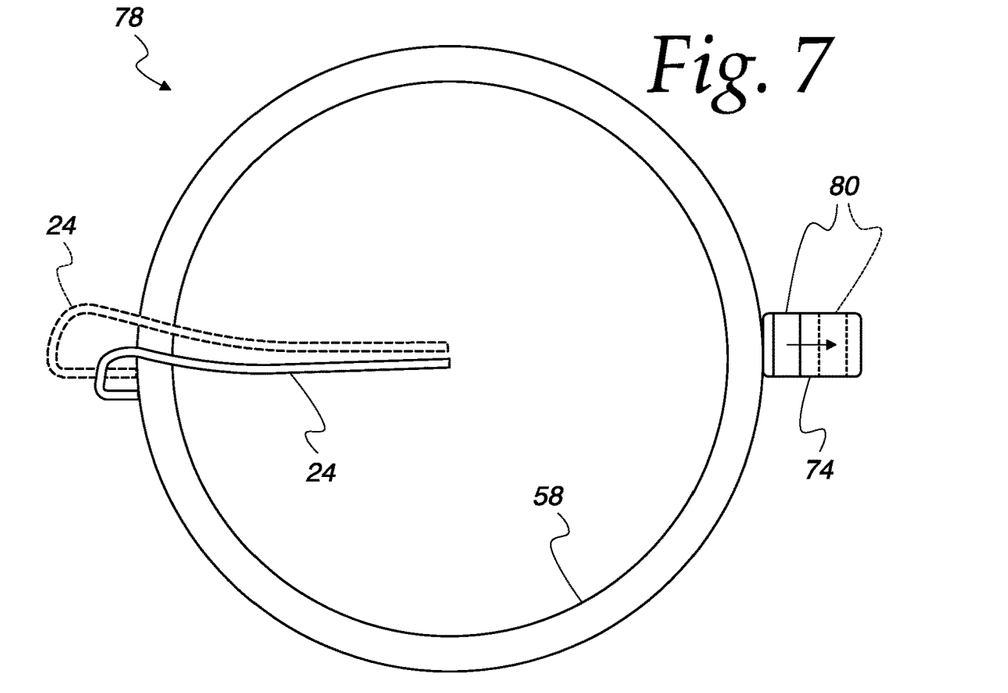
FIG. 7 illustrates the counterweight of the centrifuge assembly of FIGS. 5 and 6 moving from a radially innermost position to a radially outermost position.
Figure 8:
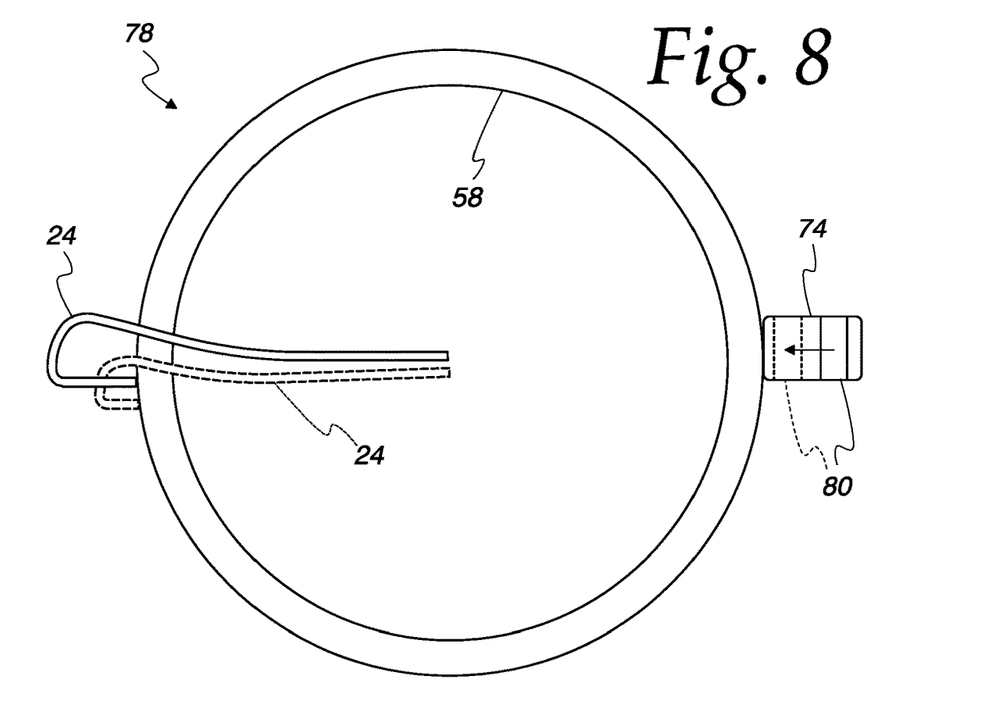
FIG. 8 illustrates the counterweight of the centrifuge assembly of FIGS. 5 and 6 moving from a radially outermost position to a radially innermost position.

As best illustrated in FIGS. 7 and 8, the radial position of the umbilicus 24 is not fixed by the bearing support 70, but may vary during the course of a procedure as the electric drive 56 rotates the yoke cross member 52 at a plurality of different rotational speeds. At a relatively low rotational speed (e.g., a minimum rotational speed), the umbilicus 24 will be positioned relatively close to the central axis 44 (as shown in solid lines in FIG. 7 and broken lines in FIG. 8), whereas the umbilicus 24 will be pulled to a position that is relatively far from the central axis 44 (as shown in broken lines in FIG. 7 and solid lines in FIG. 8) at a higher rotational speed (e.g., a maximum rotational speed).

The farther the umbilicus 24 is from the central axis 44 (i.e., at higher rotational speeds), the greater effect it will have on unbalancing the centrifuge rotor assembly 78. Accordingly, at greater rotational speeds, the counterweight 80 must be able to apply to greater counteractive force to oppose the greater tendency of the umbilicus 24 to imbalance the centrifuge rotor assembly 78. This is achieved by moving the counterweight 80 radially outwardly as the speed at which the umbilicus 24/bearing support 70 and counterweight 80 are rotated increases. In one embodiment, the counterweight 80 may be moved such that the distance between the counterweight 80 and the central axis 44 (i.e., the radial position of the counterweight 80) is the same as the distance between the central axis 44 and a particular portion of the umbilicus 24 during the entirety of a procedure. In other embodiments, the radial position of the counterweight 80 may vary with respect to the radial position of any portion of the umbilicus 24 during a procedure.

The centrifuge rotor assembly 78 may be configured such that at a minimum rotational speed (which places the umbilicus 24 at a radially innermost position, as shown in FIG. 5), the counterweight 80 is located at its radially innermost position to balance the centrifuge rotor assembly 78. Similarly, the centrifuge rotor assembly 78 may be configured such that at a maximum rotational speed (which places the umbilicus 24 at a radially outermost position, as shown in FIG. 6), the counterweight 80 is located at its radially outermost position to balance the centrifuge rotor assembly 78. At an intermediate rotational speed (which places the umbilicus 24 at a radial position between its radially innermost and outermost positions), the counterweight 80 may be located at an intermediate radial position to balance the centrifuge rotor assembly 78. The exact radial position of the counterweight 80 that balances the centrifuge rotor assembly 78 at an intermediate rotational speed may be based at least in part on the particular rotational speed. For example, if the electric drive 56 is operating to cause a rotational speed that is exactly midway between the minimum and maximum rotational speeds, then the counterweight 80 may be located at a radial position that is exactly midway between its minimum and maximum radial positions to balance the centrifuge rotor assembly 78. Alternatively, the counterweight 80 may be positioned at a different intermediate radial location at this same speed if necessary to balance the centrifuge rotor assembly 78.

Preferably, the radial position and unbalancing effect of the umbilicus 24 at a plurality of different rotational speeds are experimentally determined. With that information, the optimal radial position of the counterweight 80 may be determined for any rotational speed between the minimum and maximum rotational speeds. This information may also be used to determine the locations selected to be the radially innermost and radially outermost positions for the counterweight 80. Such an approach allows for suitable controls to be designed for automatically moving the counterweight 80 into the proper position for balancing the centrifuge rotor assembly 78 at any rotational speed.

The manner in which the counterweight 80 is moved between the radially innermost and radially outermost positions may vary. In one embodiment, the counterweight 80 is free to move radially solely under the centrifugal force applied to it by the rotating centrifuge rotor assembly 78. In this case, it may be advantageous for the counterweight 80 to be biased toward its radially innermost position, such as by providing a path that is upwardly inclined from the radially innermost position to the radially outermost position. By such a configuration, the counterweight 80 will tend to return to its radially innermost position under the force of gravity if a sufficiently strong centrifugal force is not applied to cause it to move to a more radially outward position.

Figure 9:
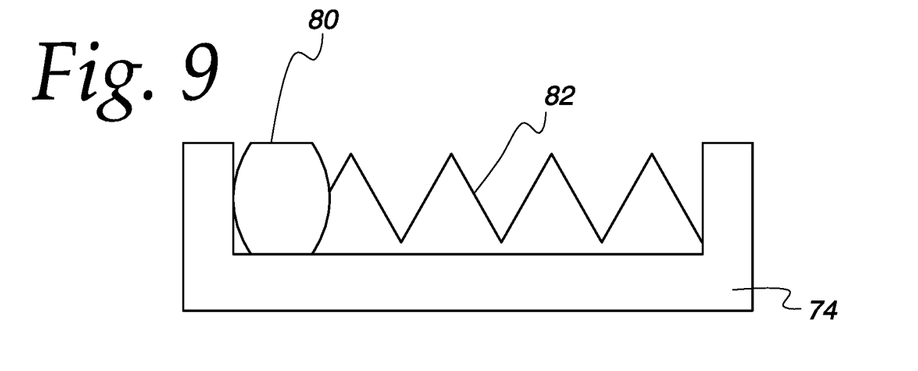
FIGS. 9 and 10 illustrate a movable counterweight employed in combination with a resilient member that biases the counterweight toward a radially innermost position.
Figure 10:
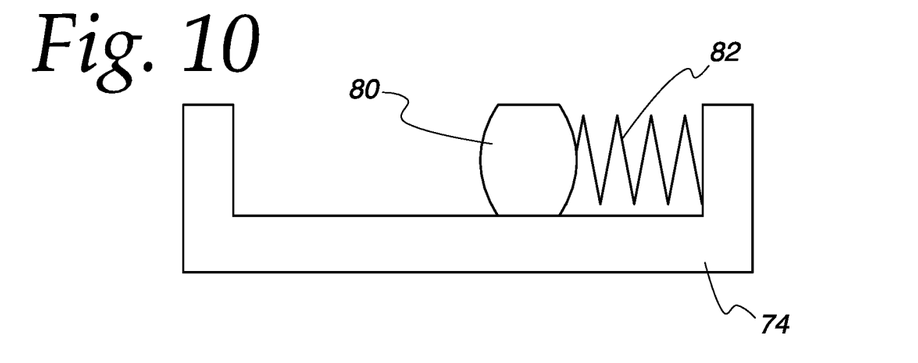

FIGS. 9 and 10 illustrate another embodiment in which the counterweight 80 is biased toward its radially innermost position (FIG. 9). In the embodiment of FIGS. 9 and 10, a resilient member 82 (e.g., a coil or helical spring) presses the counterweight 80 toward its radially innermost position. When there is not a sufficiently strong centrifugal force experienced by the counterweight 80 (e.g., when the centrifuge rotor assembly 78 is not rotating or is rotating at a minimum rotational speed), the resilient member 82 presses the counterweight 80 into its radially innermost position (FIG. 9). As the rotational speed of the centrifuge rotor assembly 78 increases, the centrifugal force experienced by the counterweight 80 increases in a direction having a radial component that opposes the force applied to the counterweight 80 by the resilient member 82. This causes the counterweight 80 to press against and compress the resilient member 82 as the counterweight 80 moves from the radially innermost position (FIG. 9) to an intermediate, more radially outward position (FIG. 10).

The resilient member 82 may be configured such that, at a maximum rotational speed, the force applied to the resilient member 82 by the counterweight 80 causes the resilient member 82 to move to a fully collapsed or compressed condition, thereby placing the counterweight 80 at its radially outermost position at the maximum rotational speed. Alternatively, the resilient member 82 may be sufficiently strong that it results in a radially outermost position of the counterweight 80 that is at a location in which the resilient member 82 is not fully collapsed or compressed. For example, depending on the strength of the resilient member 82, FIG. 10 (which shows a partially collapsed or compressed resilient member 82) may represent the radially outermost position (for a relatively strong resilient member 82) or a radially intermediate position (when the resilient member 82 is not as strong).

As the rotational speed decreases, the biasing force applied to the counterweight 80 by the resilient member 82 overcomes the force applied to the resilient member 82 by the counterweight 80, thereby causing the resilient member 82 to press the counterweight 80 to a more radially inward position until it eventually reaches its radially innermost position (FIG. 9).

In a variation of the embodiment of FIGS. 9 and 10, the positions of the counterweight 80 and the resilient member 82 may be reversed, with the resilient member 82 being positioned between the central axis 44 and the counterweight 80. In such a configuration, the resilient member 82 biases the counterweight 80 to its radially innermost position by pulling it, rather than pressing it. Thus, the resilient member 82 may be in a fully collapsed or compressed condition when the counterweight 80 is at its radially innermost position. At higher rotational speeds, the resilient member 82 is moved to a more elongated or stretched condition as the counterweight 80 moves from its radially innermost position to a more radially outward position, until the counterweight 80 reaches its radially outermost position at the maximum rotational speed. As the rotational speed decreases, the biasing force applied to the counterweight 80 by the resilient member 82 overcomes the force applied to the resilient member 82 by the counterweight 80, thereby causing the resilient member 82 to pull the counterweight 80 to a more radially inward position until the counterweight 80 eventually reaches its radially innermost position.

The characteristics of the resilient member 82 may be tailored to the needs of the system. For example, if a relatively strong biasing force must be applied to the counterweight 80 by the resilient member 82, then a spring having a relatively high spring constant may be selected. On the other hand, if a weak or moderate biasing force is to be applied to the counterweight 80 by the resilient member 82, then a spring having a lower spring constant may be employed. If a variable biasing force is required, then a suitably configured resilient member 82 (e.g., a spring having a varying pitch) may be selected. Other variations to the resilient member 82 (which may include the provision of a plurality of resilient members 82) may also be practiced without departing from the scope of the present disclosure.

Figure 11:
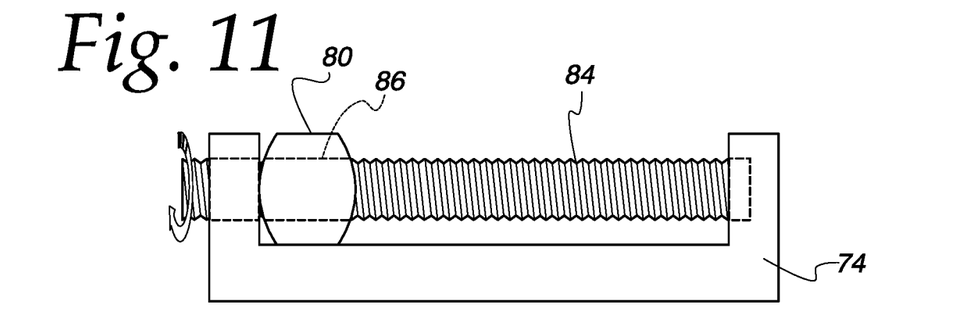
FIGS. 11 and 12 illustrate a movable counterweight employed in combination with an electrically driven positioning member.
Figure 12:
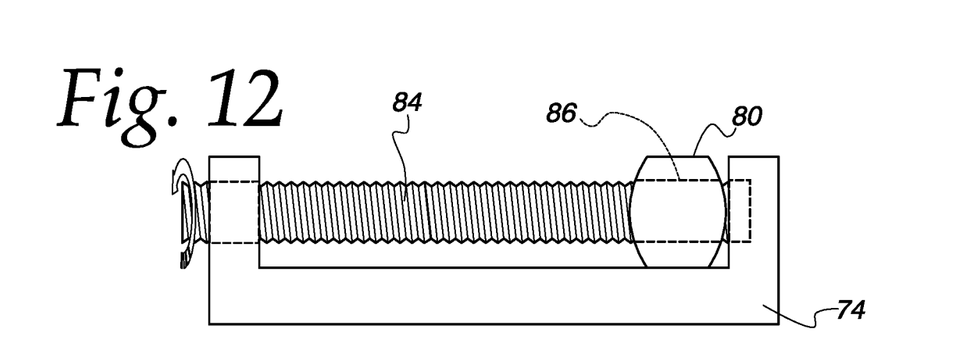

FIGS. 11 and 12 illustrate an alternative embodiment, which does not bias the counterweight 80 to any particular position, but instead is configured to selectively move the counterweight 80 to any position at any time. In the embodiment of FIGS. 11 and 12, the counterweight 80 is provided in combination with an electrically driven positioning member 84. The positioning member 84 is illustrated as an externally threaded screw or shaft of an electrical worm drive servo, but it should be understood that the positioning member 84 and associated system for operating the positioning member 84 to move the counterweight 80 may be variously configured without departing from the scope of the present disclosure.

In the illustrated embodiment, the positioning member 84 passes through an internally threaded bore 86 of the counterweight 80, with the external threads of the positioning member 84 mating with the internal threads of the bore 86. As the positioning member 84 is rotated about its central axis, the mating threads cause the counterweight 80 to move along the length of the positioning member 84 between a radially innermost position (FIG. 11) to a radially outermost position (FIG. 12). Rotating the positioning member 84 in one direction causes the counterweight 80 to move to a more radially outward position, while rotating the positioning member 84 in the opposite direction causes the counterweight 80 to move to a more radially inward position. When the counterweight 80 has been moved to the proper radial location, rotation of the positioning member 84 may cease to maintain the counterweight 80 in the proper location.

The positioning member 84 may be associated with the electric drive 56 in a manner that allows the operation of the positioning member 84 to be at least partially dependent upon the operation of the electric drive 56. For example, a controller or intermediary device may monitor the rotational speed at which the electric drive 56 rotates the centrifuge rotor assembly 78. The intermediary device may then cause the positioning member 84 to be rotated (e.g., by issuing commands to an electrical worm drive servo of which the positioning member 84 is a component) to move the counterweight 80 to the proper radial location to balance the centrifuge rotor assembly 78. If the intermediary device determines that the electric drive 56 is operating at a minimum rotational speed, then it may cause the positioning member 84 to move the counterweight 80 to its radially innermost position (FIG. 11) to balance the centrifuge rotor assembly 78. If the intermediary device determines that the electric drive 56 is operating at a maximum rotational speed, then it may cause the positioning member 84 to move the counterweight 80 to its radially outermost position (FIG. 12) to balance the centrifuge rotor assembly 78. If the intermediary device determines that the electric drive 56 is operating at an intermediate rotational speed, then it may cause the positioning member 84 to move the counterweight 80 to the appropriate radial position between the radially innermost and radially outermost positions to balance the centrifuge rotor assembly 78 (with the relationship between rotational speed and the radial position of the counterweight 80 being experimentally determined during manufacture and/or calibration of the system 10). The intermediary device or an associated device may be provided with additional functionality (e.g., one or more sensors that detect an imbalance of the centrifuge rotor assembly 78 that may be different from the effect expected at a particular rotational speed) that may be used to fine-tune the operation of the positioning member 84 and adjust the counterweight 80 to the optimal radial position.

Aspects of the present subject matter described above may be beneficial alone or in combination with one or more other aspects. Without limiting the foregoing description, in accordance with one aspect of the subject matter herein, there is provided a centrifuge rotor assembly. The centrifuge rotor assembly includes a chamber assembly having a central axis and configured to receive at least a portion of a processing chamber of a fluid circuit. The centrifuge rotor assembly also includes a bearing support and a counterweight. The bearing support is configured to receive a portion of an umbilicus fluidly connected to the processing chamber, while the counterweight is positioned substantially diametrically opposed to the bearing support with respect to the chamber assembly. An electric drive is configured to rotate the bearing support and the counterweight about the central axis at a plurality of different rotational speeds, with the bearing support and the counterweight being configured to remain substantially diametrically opposed to each other with respect to the chamber assembly during rotation of the bearing support and the counterweight about the central axis. The counterweight is automatically movable with respect to the bearing support between a radially innermost position and a radially outermost position during rotation of the bearing support and the counterweight about the central axis, with the position of the counterweight depending at least in part on the rotational speed at which the bearing support and the counterweight are rotated about the central axis.

In accordance with another aspect which may be used or combined with the preceding aspect, the counterweight is configured to be positioned at its radially outermost position when the electric drive is rotating the bearing support and the counterweight about the central axis at a maximum rotational speed.

In accordance with another aspect which may be used or combined with any of the preceding aspects, the counterweight is configured to be positioned at its radially innermost position when the electric drive is rotating the bearing support and the counterweight about the central axis at a minimum rotational speed.

In accordance with another aspect which may be used or combined with any of the preceding aspects, the counterweight is configured to be positioned between its radially innermost and radially outermost positions when the electric drive is rotating the bearing support and the counterweight about the central axis at a rotational speed between a maximum rotational speed and a minimum rotational speed.

In accordance with another aspect which may be used or combined with any of the preceding aspects, there is provided a yoke cross member including a pair of wing plates. The bearing support is associated with one of the wing plates and the counterweight is associated with the other wing plate.

In accordance with another aspect which may be used or combined with any of the preceding aspects, there is provided a resilient member associated with the counterweight and configured to bias the counterweight toward its radially innermost position.

In accordance with another aspect which may be used or combined with the preceding aspect, the resilient member is a spring.

In accordance with another aspect which may be used or combined with any of the first five aspects, there is provided an electrically driven positioning member associated with the counterweight and operable to move the counterweight between its radially innermost and radially outermost positions.

In accordance with another aspect which may be used or combined with the preceding aspect, the positioning member comprises an electrical worm drive servo.

In accordance with another aspect which may be used or combined with any of the preceding aspects, the counterweight is infinitely positionable between its radially innermost and radially outermost positions.

In accordance with another aspect which may be used or combined with any of the first nine aspects, the counterweight is positionable in a defined number of positions between the radially innermost and radially outermost positions.

In accordance with another aspect, there is provided a method of operating a centrifuge rotor assembly comprising a chamber assembly having a central axis and receiving at least a portion of a processing chamber of a fluid circuit, a bearing support receiving a portion of an umbilicus fluidly connected to the processing chamber, and a counterweight positioned substantially diametrically opposed to the bearing support with respect to the chamber assembly. The method includes rotating the bearing support and the counterweight about the central axis at a first rotational speed while the bearing support and the counterweight remain substantially diametrically opposed to each other with respect to the chamber assembly. The rotational speed is changed from the first rotational speed to a second rotational speed while the bearing support and the counterweight remain substantially diametrically opposed to each other with respect to the chamber assembly. Changing the rotational speed to the second rotational speed includes automatically moving the counterweight with respect to the bearing support from a first radial position to a second radial position, with the radial position of the counterweight depending at least in part on the rotational speed at which the bearing support and the counterweight are rotated about the central axis.

In accordance with another aspect which may be used or combined with the preceding aspect, changing the rotational speed to the second rotational speed includes increasing the rotational speed, with the second radial position being farther from the central axis than the first radial position.

In accordance with another aspect which may be used or combined with the preceding aspect, the second rotational speed is a maximum rotational speed and the second radial position is a radially outermost position.

In accordance with another aspect which may be used or combined with any of the preceding two aspects, the first rotational speed is a minimum rotational speed and the first radial position is a radially innermost position.

In accordance with another aspect which may be used or combined with the twelfth or thirteenth aspects, at least one of the first and second rotational speeds is between a minimum rotational speed and a maximum rotational speed, with the radial position of the counterweight when the bearing support and the counterweight are being rotated about the central axis at that rotational speed being between a radially innermost position and a radially outermost position.

In accordance with another aspect which may be used or combined with any of the thirteenth through sixteenth aspects, automatically moving the counterweight with respect to the bearing support from a first radial position to a second radial position includes overcoming a biasing force applied to the counterweight by a resilient member.

In accordance with another aspect which may be used or combined with the twelfth aspect, changing the rotational speed to a second rotational speed includes decreasing the rotational speed, with the second radial position being closer to the central axis than the first radial position.

In accordance with another aspect which may be used or combined with the preceding aspect, the first rotational speed is a maximum rotational speed and the first radial position is a radially outermost position.

In accordance with another aspect which may be used or combined with any of the preceding two aspects, the second rotational speed is a minimum rotational speed and the second radial position is a radially innermost position.

In accordance with another aspect which may be used or combined with the eighteenth aspect, at least one of the first and second rotational speeds is between a minimum rotational speed and a maximum rotational speed, with the radial position of the counterweight when the bearing support and the counterweight are being rotated about the central axis at that rotational speed being between a radially innermost position and a radially outermost position.

In accordance with another aspect which may be used or combined with any of the preceding four aspects, automatically moving the counterweight with respect to the bearing support from the first radial position to the second radial position includes moving the counterweight under the influence of a biasing force applied to the counterweight.

In accordance with another aspect which may be used or combined with any of the twelfth through twenty-second aspects, automatically moving the counterweight with respect to the bearing support from the first radial position to the second radial position includes moving the counterweight using an electrically driven positioning member.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A centrifuge rotor assembly comprising:
    a chamber assembly having a central axis and configured to receive at least a portion of a processing chamber of a fluid circuit;
    a bearing support configured to receive a portion of an umbilicus fluidly connected to the processing chamber;
    a counterweight positioned substantially diametrically opposed to the bearing support with respect to the chamber assembly; and
    an electric drive configured to rotate the bearing support and the counterweight about the central axis at a plurality of different rotational speeds, wherein
       the bearing support and the counterweight are configured to remain substantially diametrically opposed to each other with respect to the chamber assembly during rotation of the bearing support and the counterweight about the central axis,
       the counterweight is automatically movable with respect to the bearing support between a radially innermost position and a radially outermost position during rotation of the bearing support and the counterweight about the central axis,
       the position of the counterweight depends at least in part on the rotational speed at which the bearing support and the counterweight are rotated about the central axis, and
       the counterweight is configured to automatically move to a different radial position during rotation of the bearing support and the counterweight about the central axis in response to a change in the radial and/or axial position of at least a portion of the umbilicus with respect to the central axis.

2. The centrifuge rotor assembly of claim 1, wherein the counterweight is configured to be positioned at said radially outermost position when the electric drive is rotating the bearing support and the counterweight about the central axis at a maximum rotational speed.

3. The centrifuge rotor assembly of claim 1, wherein the counterweight is configured to be positioned at said radially innermost position when the electric drive is rotating the bearing support and the counterweight about the central axis at a minimum rotational speed.

4. The centrifuge rotor assembly of claim 1, wherein the counterweight is configured to be positioned between said radially innermost position and said radially outermost position when the electric drive is rotating the bearing support and the counterweight about the central axis at a rotational speed between a maximum rotational speed and a minimum rotational speed.

5. The centrifuge rotor assembly of claim 1, further comprising a yoke cross member including a pair of wing plates, wherein the bearing support is associated with one of the wing plates and the counterweight is associated with the other one of the wing plates.

6. The centrifuge rotor assembly of claim 1, further comprising a resilient member associated with the counterweight and configured to bias the counterweight toward the radially innermost position.

7. The centrifuge rotor assembly of claim 6, wherein said resilient member comprises a spring.

8. The centrifuge rotor assembly of claim 1, further comprising an electrically driven positioning member associated with the counterweight and operable to move the counterweight between the radially innermost and radially outermost positions.

9. The centrifuge rotor assembly of claim 8, wherein the positioning member comprises an electrical worm drive servo.

10. The centrifuge rotor assembly of claim 1, wherein the counterweight is infinitely positionable between the radially innermost and radially outermost positions.

11. The centrifuge rotor assembly of claim 1, wherein the counterweight is positionable in a defined number of positions between the radially innermost and radially outermost positions.

12. A centrifuge rotor assembly comprising:
    a chamber assembly having a central axis and configured to receive at least a portion of a processing chamber of a fluid circuit;
    a bearing support configured to receive a portion of an umbilicus fluidly connected to the processing chamber;
    a counterweight positioned substantially diametrically opposed to the bearing support with respect to the chamber assembly; and
    an electric drive configured to rotate the bearing support and the counterweight about the central axis at a plurality of different rotational speeds, wherein
       the bearing support and the counterweight are configured to remain substantially diametrically opposed to each other with respect to the chamber assembly during rotation of the bearing support and the counterweight about the central axis,
       the counterweight is automatically movable along a counterweight support with respect to the bearing support between a radially innermost position and a radially outermost position during rotation of the bearing support and the counterweight about the central axis,
       the position of the counterweight depends at least in part on the rotational speed at which the bearing support and the counterweight are rotated about the central axis, and
       the counterweight is movable along the counterweight support in a direction having an axial component defined by the counterweight support when moving to a more radially outward position and/or to a more radially inward position.

13. The centrifuge rotor assembly of claim 12, wherein the counterweight is configured to be positioned between said radially innermost position and said radially outermost position when the electric drive is rotating the bearing support and the counterweight about the central axis at a rotational speed between a maximum rotational speed and a minimum rotational speed.

14. The centrifuge rotor assembly of claim 12, further comprising a yoke cross member including a pair of wing plates, wherein the bearing support is associated with one of the wing plates and the counterweight is associated with the other one of the wing plates.

15. The centrifuge rotor assembly of claim 12, further comprising a resilient member associated with the counterweight and configured to bias the counterweight toward the radially innermost position.

16. The centrifuge rotor assembly of claim 12, further comprising an electrically driven positioning member associated with the counterweight and operable to move the counterweight between the radially innermost and radially outermost positions.

17. The centrifuge rotor assembly of claim 12, wherein the counterweight is infinitely positionable between the radially innermost and radially outermost positions.

18. A centrifuge rotor assembly comprising:
a chamber assembly having a central axis and configured to receive at least a portion of a processing chamber of a fluid circuit;
a bearing support configured to receive a portion of an umbilicus fluidly connected to the processing chamber;
a counterweight positioned substantially diametrically opposed to the bearing support with respect to the chamber assembly; and
an electric drive configured to rotate the bearing support and the counterweight about the central axis at a plurality of different rotational speeds, wherein
the bearing support and the counterweight are configured to remain substantially diametrically opposed to each other with respect to the chamber assembly during rotation of the bearing support and the counterweight about the central axis,
the counterweight is automatically movable along a counterweight support with respect to the bearing support between a radially innermost position and a radially outermost position during rotation of the bearing support and the counterweight about the central axis,
the position of the counterweight depends at least in part on the rotational speed at which the bearing support and the counterweight are rotated about the central axis, and
the counterweight is movable along a non-linear path defined by the counterweight support when moving between the radially innermost position and the radially outermost position.

19. The centrifuge rotor assembly of claim 18, wherein the counterweight is configured to be positioned between said radially innermost position and said radially outermost position when the electric drive is rotating the bearing support and the counterweight about the central axis at a rotational speed between a maximum rotational speed and a minimum rotational speed.

20. The centrifuge rotor assembly of claim 18, further comprising a yoke cross member including a pair of wing plates, wherein the bearing support is associated with one of the wing plates and the counterweight is associated with the other one of the wing plates.

21. The centrifuge rotor assembly of claim 18, further comprising a resilient member associated with the counterweight and configured to bias the counterweight toward the radially innermost position.

22. The centrifuge rotor assembly of claim 18, further comprising an electrically driven positioning member associated with the counterweight and operable to move the counterweight between the radially innermost and radially outermost positions.

23. The centrifuge rotor assembly of claim 18, wherein the counterweight is infinitely positionable between the radially innermost and radially outermost positions.

* * * * *